United States Patent [19]
Gabbay

[11] Patent Number: 4,802,477
[45] Date of Patent: Feb. 7, 1989

[54] STERNUM CLOSURE DEVICE

[76] Inventor: Shlomo Gabbay, 1 Randall Dr., Short Hills, N.J. 07078

[21] Appl. No.: 47,869

[22] Filed: May 7, 1987

[51] Int. Cl.⁴ ..................... A61B 17/08; A61B 17/14
[52] U.S. Cl. .................................. 128/317; 128/334 R
[58] Field of Search ............ 128/317, 92 VZ, 334 R, 128/334 C, 335

[56] References Cited

U.S. PATENT DOCUMENTS

| | | | |
|---|---|---|---|
| 184,804 | 11/1876 | Stohlmann | 128/317 |
| 2,342,695 | 2/1944 | Rinaldy | 128/317 |
| 4,279,248 | 7/1981 | Gabbay | 128/346 X |

*Primary Examiner*—Michael H. Thaler
*Attorney, Agent, or Firm*—Jordan B. Bierman

[57] ABSTRACT

A method and device for securing a sternum in closed position comprising a plurality of fastening clamps which are spaced apart along an incision. Each of the fastening clamps is anchored to the sternum on both sides of the incision and has a lower section which is beneath the sternum and an upper section on the upper side of the sternum. A flexible saw is provided beneath the sternum, between the lower sections of the fastening clamps and the lower side of the sternum. The saw extends approximately along the line of the incision, and the sternum is reopened by grasping the ends of the flexible saw and causing it to reciprocate, thus opening the sternum quickly and minimizing morbidity.

32 Claims, 4 Drawing Sheets

STERNUM CLOSURE DEVICE

The present invention is directed to an improved sternum closure device, especially one which permits easy and safe reopening.

The present invention is intended for the same general field of use as that disclosed and claimed in my prior U.S. Pat. No. 4,279,248, issued July 21, 1981. There are approximately 200,000 sternotomy operations performed in the United States each year. Of these, approximately 35,000 to 40,000 are reopenings. The prior art devices, which generally comprise clamps and/or wires, do not facilitate these reopenings in any way. In actuality, the scar tissue which builds up around the clamps or wires presents serious difficulties to the surgeon. The heart is, of course, located directly beneath the sternum which bows outwardly from top to bottom. Should the surgeon not be sufficiently dexterous, there is a real risk of puncturing this vital organ. At best, it is time consuming, which increases the risks of morbidity.

The present invention is intended to solve this problem. In its broadest aspect, it comprises a device for securing the sternum in a closed position after opening. The device comprises a plurality of fastening means which are spaced apart along the line of the incision. Each fastening means is anchored to the sternum on both sides of the incision and each fastening means is provided with a lower section which extends beneath the sternum and an upper section which is located on the upper side of the sternum. A flexible saw is located beneath the sternum and is held between the lower sections and the lower side of the sternum. Preferably, the saw is an abrasive wire (e.g. a Gigli saw) and is long enough so that the extremities can be brought around the edges of the sternum and/or ribs and secured at the upper side of the sternum. This can be done by simply suturing the extremeties to the tissue or by clamping them between at least one of the upper sections and the upper side of the sternum.

Thus, when a reopening is necessary, the surgeon need only loosen or cut away the fastening means which holds the ends of the saw, cut away and remove the upper sections, reciprocate the saw manually, thereby cutting through the sternum. As can easily be seen, the lower sections of the fastening means hold the saw against the lower side of the sternum, thereby preventing any real opportunity for puncture or other injury to the heart; a maneuver that takes no more than 30 seconds compared to at least 30 to 60 minutes for reopening the sternum in the conventional manner.

In a preferred form of the device, each of the lower sections comprises a lower grip which is adapted to extend across the incision and which has a lower gripping means adapted to engage the lower side of the sternum. Similarly, each of the upper sections comprises an upper grip also adapted to extend across the incision and which has an upper gripping means adapted to engage the upper side of the sternum. Each pair of lower and upper grips has a stem with its lower end adapted to engage the lower grip. The stem, when in place, will project through the sternum, preferably at the incision, and also through the upper grip. A means is provided on the stem for urging the lower grip and upper grip into clamping relationship with the sternum.

In a particularly advantageous form of the device, the stem is threaded and a nut is provided on the stem, above the upper grip. When the stem and nut are turned relative to one another, the upper and lower grips are drawn towards each other, clamping the sternum therebetween.

In a most preferable form of the device, at least the upper grips are of disk-like shape having a bridge extending arcuately upwards therefrom. At approximately the uppermost point of the bridge, there is provided an opening which engages the external threads on the stem. The lower grips, which may also be of similar circular form, are also provided with openings through which the stem passes. However, these openings do not engage the threads (or the stem has no threads at this point), so that the stem is freely rotatable relative to the lower grips.

In this arrangement, it is unnecessary to provide a nut in order to draw the upper and lower grips together. It is only necessary to turn the stem, thereby causing the upper grip to approach its corresponding lower grip until the sternum is securely clamped therebetween.

It has been found desirable to provide each stem with a loop at its upper end. A rod passes through the loop of each such stem, thereby allowing the number and spacing of the clamps to be adjusted prior to insertion into the body.

After closure and clamping of the sternum, the portions of the stem (includng the loops, if present) which extend above the nut or above the bridge (as the case may be) are cut off and discarded.

In carrying out the present invention, the edges of the opened sternum ae brought into juxtaposition in any known manner, such as by the use of a sternal approximator. Each fastening means (such as a wire) is then applied to both sides of the incision to form the lower sections. The saw is then placed on the lower sections, the sternum brought to the fully closed position, the ends of the saw brought around the edges of the sternum and laid flat against the upper side thereof, and the upper sections of the fastening means are secured. The ends can be clamped or retained in place by any means, including the use of one or more upper sections of the fastening means.

In the event that clamps are used instead of the wires described above, they are preferably placed on a rod which passes through the loops at the upper ends of the stems. They are then arranged on the rod in accordance with the size the configuration of the patient. When the approximators are in place, the lower grips of the clamps are located beneath the sternum. The saw is then laid on the lower grips, preferably in a groove cut therein for this purpose. The approximators are then tightened and the edges of the incision brought into contact with each other. The nuts can then be tightened so that the upper and lower grips are brought into the desired clamping relationship with the sternum. At the same time, the ends of the saw can be brought around the seernum edges and inserted under the upper grips of one or more of the clamps. Alternatively, they can be secured adjacent the upper side of the sternum by other clamping or suturing means.

A further modification of the present invention makes liberal use of absorbable surgical polymers. Such polymers are well known in the art and are exemplified by Dexon, a product of Davis and Geck. In this modification, the body absorbs all or part of the implants after a period sufficient to permit natural healing of the incision. If desired, portions of the device which require greater strength may be made of metal set into the absorbable polymer. For example, the portions of the grips which engage threads on the stem may advantageously be of metal. Similarly, the stem itself can also be metal. In this form of the invention, it is particularly easy to reopen the sternum as the various grips will have been absorbed and need not be removed, thus simplifying the procedure.

A further advantage has been found in coating the flexible saw with the same absorbable polymer. It is recognized that, when the body absorbs the polymer, it deposits (usually fibrous) tissue in place thereof; this provides a coating for the saw. As a result, the sharp teeth would be "blunted" by the tissue. Thus, when it is time to reopen, reciprocation of the saw is less likely to injure the heart or any of the major arteries. At points at which the saw comes into contact with the sternum (which is relatively hard), the fibrous tissue will be scraped off readily and the teeth exposed to perform their cutting function.

In the accompanying drawings, constituting a part hereof, and in which like reference characters indicate like parts, FIG. 1 shows an exposed sternum which has been opened and closed with clamps of the present invention, including the flexible saw;

Figure 3:
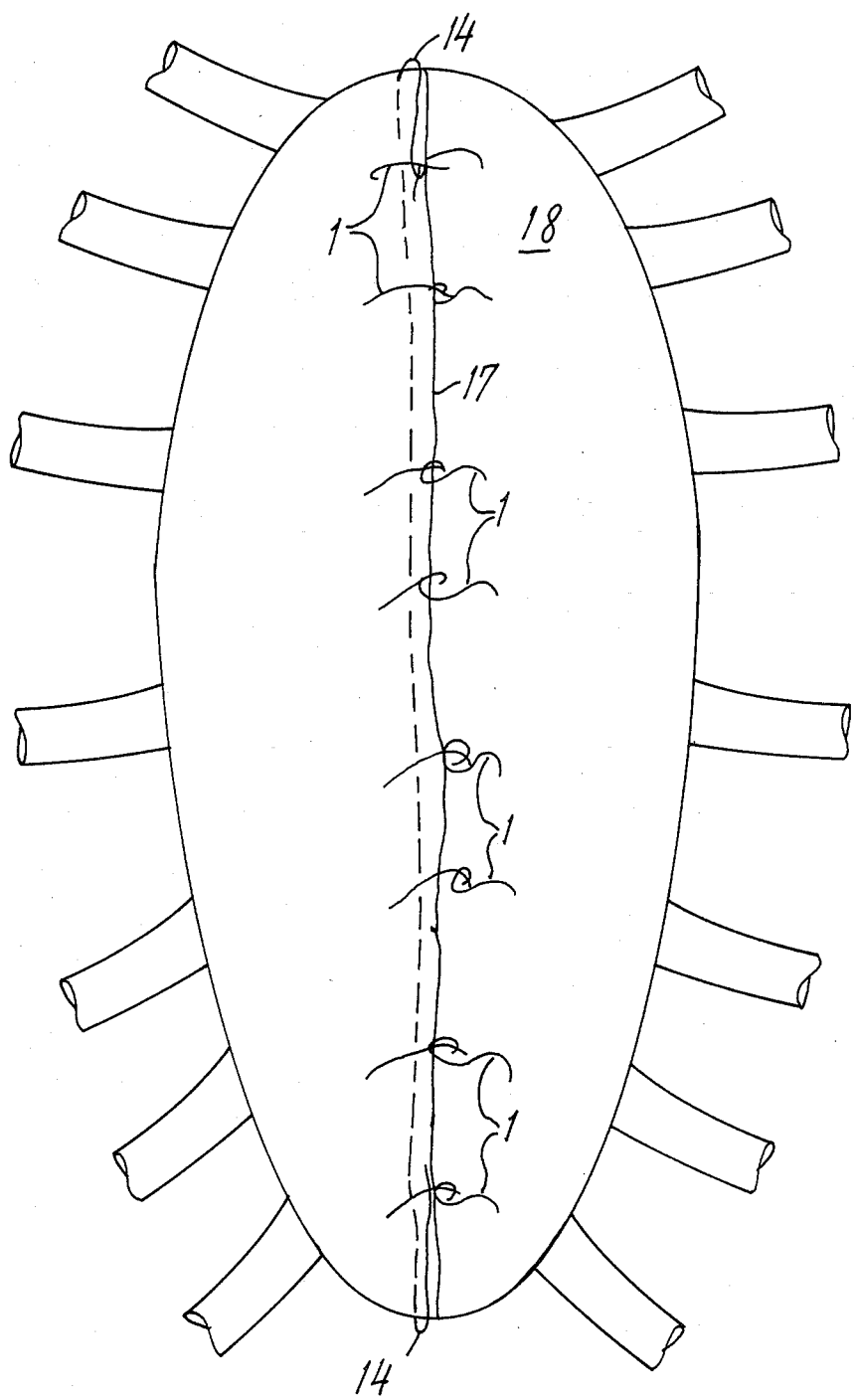
FIG. 3 is a view similar to that of FIG. 1 wherein the sternum is held together with wires.
Figure 4:
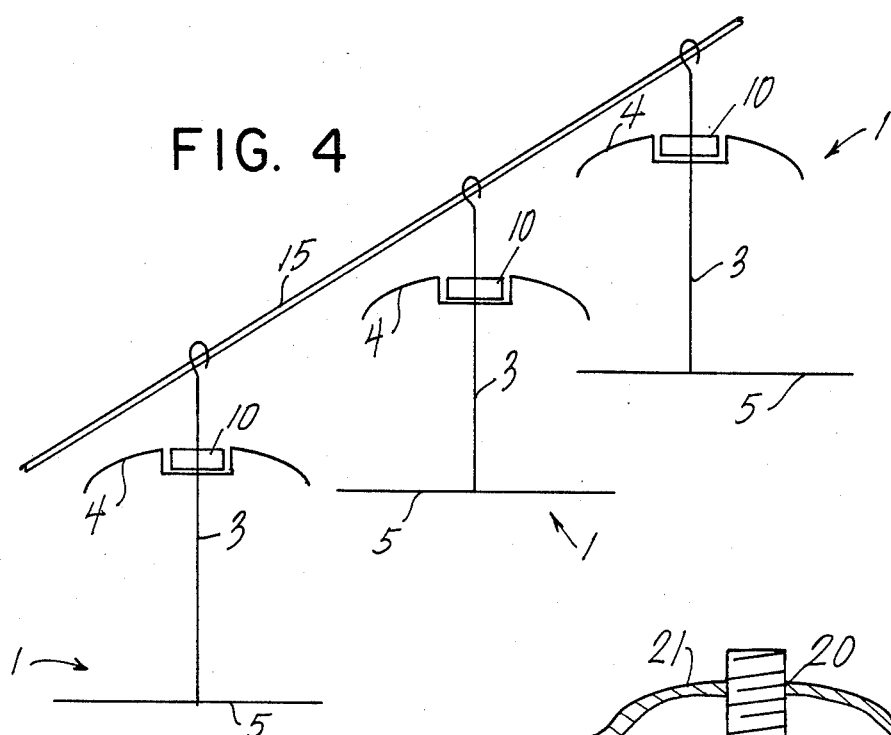
FIG. 4 is a schematic view showing a plurality of clamps located on the removable rod.

FIG. 3 shows the sternum after it has been opened and closed in accordance with the present invention. Sternum 18 has incision 17 which has been drawn together with approximators (not shown). Wires 1 serve to retain the sternum in proper position for healing. Beneath the sternum and resting on the lower sections of wires 1 is flexible saw 14. The ends thereof extend over the edges of the sternum and are fixed beneath the outermost wires 1.

Thus, when the chest cavity is to be reopened, the outermost wires 1 are loosened and the ends of saw 14 removed. These ends are then reciprocated, causing saw 14 to cut through sternum 18.

Figure 1:
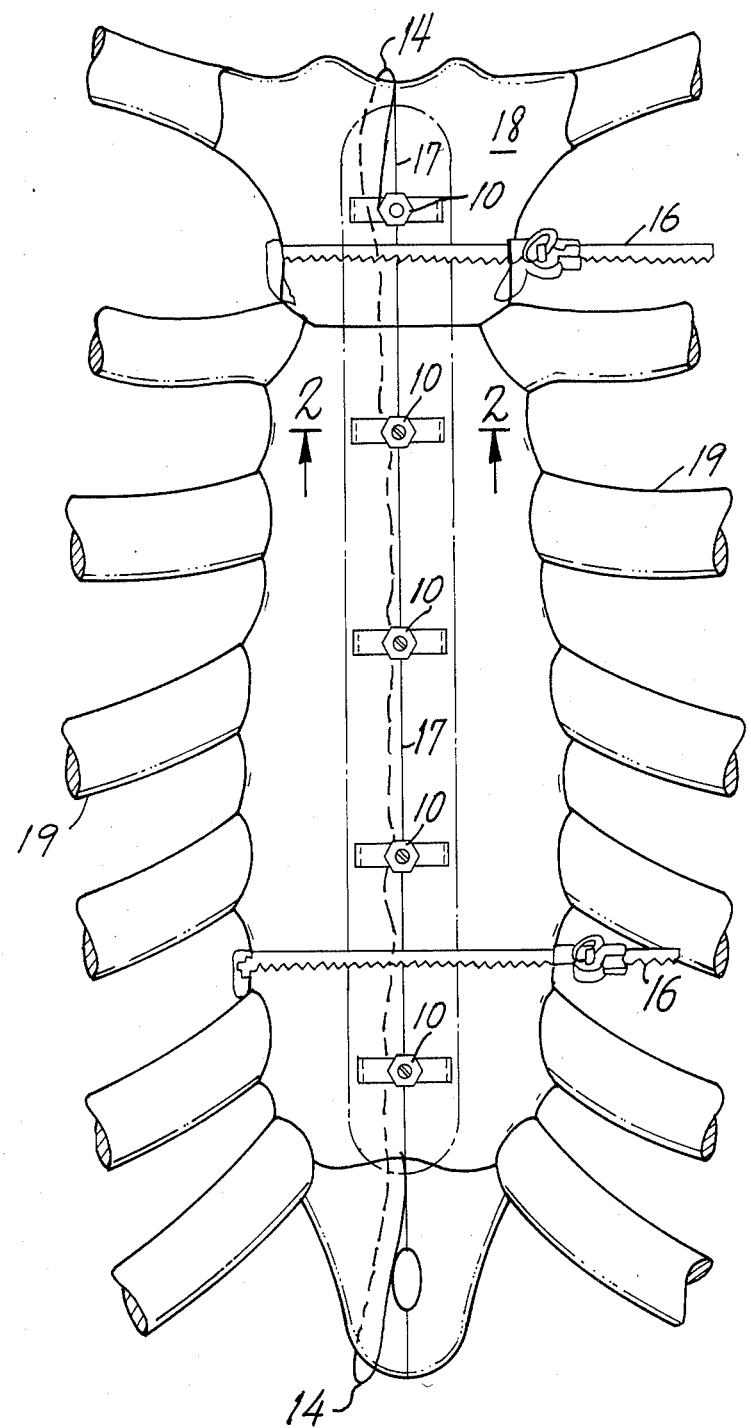
Figure 2:
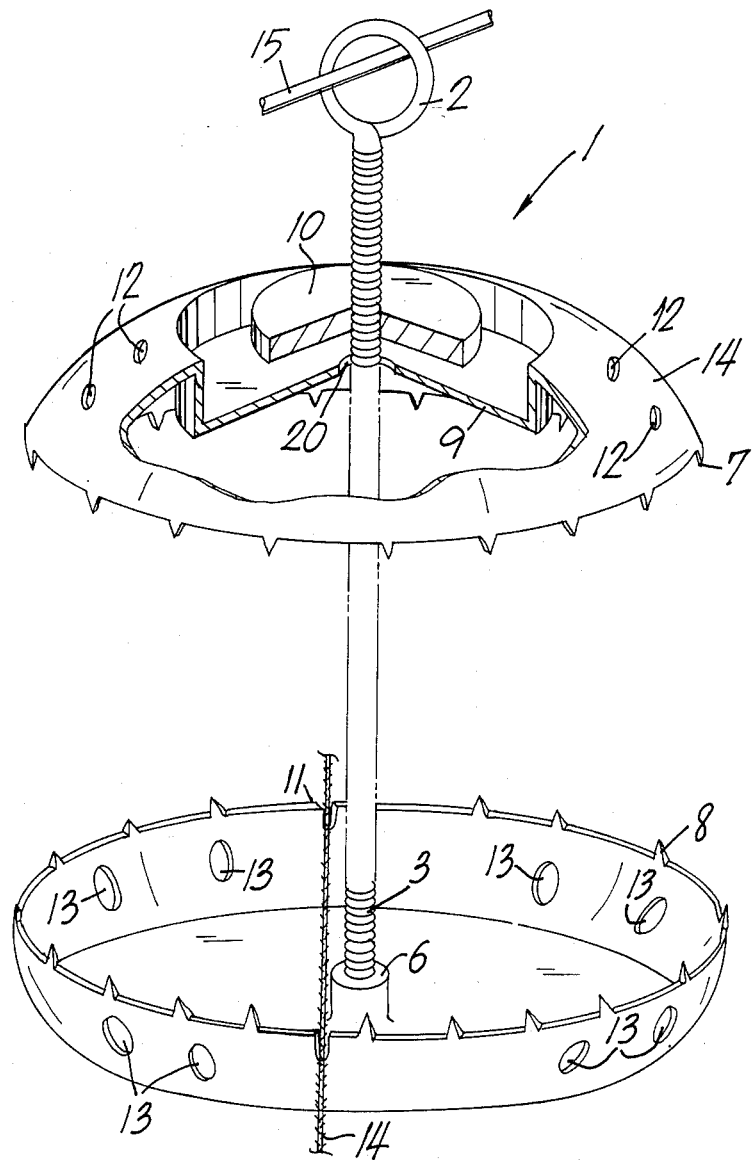
FIG. 2 is an enlarged view, partly in section and of a clamp in accordance with the present invention.

A preferred form of fastening means is shown in FIG. 2. Clamp 1 is provided with lower grip 5, upper grip 4 and stem 3. The lower end of stem 3 engages lower grip 5 and extends upwardly through collar 20 of upper grip 4. Part of upper grip 4 constitutes receiver 9, in which nut 10 is located. The threads on stem 3 are engaged by corresponding threads on nut 10, thereby providing the means for urging upper grip 4 and lower grip 5 into clamping relationship with sternum 18 (see FIG. 1). Upper grip 4 is provided with a plurality of upper teeth 7 and, correspondingly, lower grip 5 is provided with a plurality of lower teeth 8.

Grooves 11 in lower grip 5 receive flexible saw 14. Upper holes 12 and lower holes 13 are provided in upper grip 4 and lower grip 5, respectively. Lower grip 5 also comprises threaded holder 6 into which stem 3 is inserted.

In use, the edges of the incision are brought into juxtaposition by approximators 16. Then, a suitable number (depending upon the size and configuration of the patient) of clamps 1 placed on rod 15. They are then spaced apart in a manner suited to the particular patient.

Lower grips 5 are then inserted between the edges of the incision and saw 14 is placed thereon in grooves 11. When tension is placed on saw 14, its interaction with grooves 11 will tend to cause lower grips 5 to assume a position extending substantially on either side of incision 17. By tightening approximators 16, the edges of incision 17 are brought substantially into contact. Nuts 10 are then tightened so that sternum 18 is clamped between lower grip 5 and upper grip 4 along the length of incision 17. If desired, the end clamps 1 can be left somewhat loose to permit the ends of saw 14 to be inserted under upper grips 4. These are then tightened and the ends of saw 14 are thereby secured. Rod 15 is removed and loops 2 and any unneeded portions of stem 3 extending above upper grip 4 are cut off and discarded.

Alternatively, it is advantageous to simply suture the extremeties of the flexible saw to tissue adjacent the upper side of the sternum. In such a case, it is, of course, unnecessary to clamp the extremeties between the upper grips and the sternum.

In reopening the incision, all the upper grips are removed and the ends of saw 14 released. By manipulation of the ends, saw 14 is caused to reciprocate, thereby either reopening incision 17 or making a new incision nearby.

Figure 5:
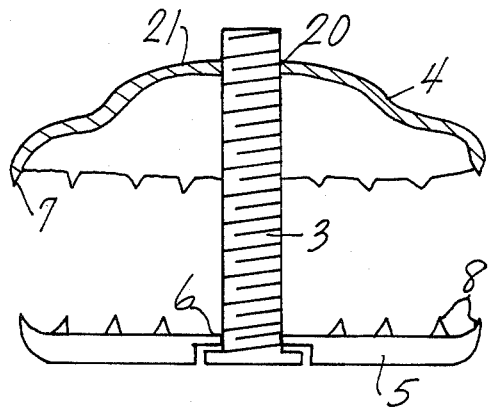
FIG. 5 is a view similar to that of FIG. 2 showing the modified form of the upper grip.
Figure 6:
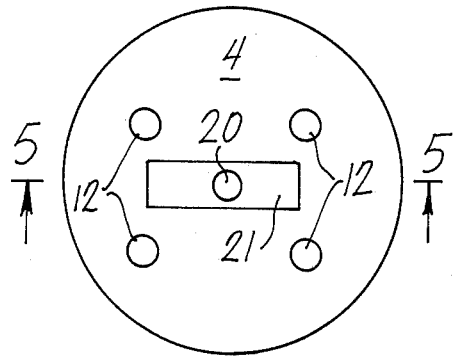
FIG. 6 is a plan view of the modified form of the upper grip.
Figure 7:
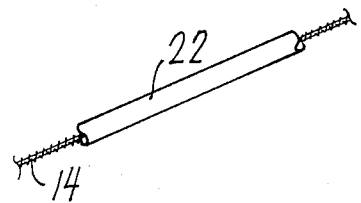
FIG. 7 is a view showing the flexible saw located within a sheath.

A modified and especially advantageous form of the device is shown in FIGS. 5 and 6. As can be seen therefrom, upper grip 4 comprises a generally circular base having bridge 21 extending arcuately upward therefrom. Upper holes 12 are provided for diffusion of nutrients in order to reduce the possibility of infection. Collar 20 is provided on bridge 21 and is adapted to engage the threads on stem 3. Lower grip 5 is mounted on the lower end of stem 3 so that stem 3 is freely rotatable with respect thereto.

In this case, it is only necessary to rotate stem 3 in order to bring upper grip 4 into pressure relationship with the sternum and lower grip 5. No clamping nut is necessary. As in the other forms of the invention, the excess stem projecting above upper grip 4 in its clamped position is cut off and discarded.

In reopening, it is only necessary to cut bridge 20 and remove upper grip 4 before loosening saw 14 and causing it to reciprocate. As has been previously explained, the saw will then either reopen incision 17 or make a new incision nearby. In this form of the invention, it is preferred that upper grip 4 be made of the aforementioned absorbable polymer. Since bridge 21 is easily cut off, the metal upper grip 4 can readily be removed. Therefore, the use of absorbable polymer is of less importance in this modification. As a result of the present invention, reopening can be carried out in a matter of seconds, rather than approximately one hour as is required by prior art methods and devices.

It is to be understood that such variations as would be apparent to the person of ordinary skill in the art can be made without departing from the present invention. For example, the clamps can be of a wide variety of configurations, including those described in my U.S. Pat. No. 4,279,284, previously mentioned. Flexible saw 14 may be placed inside sheath 22 which, in turn, is located in grooves 11 and 23. Sheath 22 would extend substantially the length of incision 17 and the extremeties of saw 14 would extend beyond the ends of sheath 22. This enables the reopening surgeon to easily grasp the saw and reciprocate it.

These and other changes may be made in the invention without departing from the scope or spirit thereof. The invention is to be broadly construed, and not to be limited except by the character of the claims appended hereto.

I claim:

1. A combination of a saw and a device for securing a sternum in a closed position after opening, said sternum having an upper side and a lower side, said device comprising a plurality of fastening means adapted to be spaced apart along an incision, each of said fastening means adapted to be anchored to said sternum on both sides of said incision and at least some of said fastening means having lower sections adapted to be beneath said sternum and also having upper sections adapted to be on said upper side of said sternum, each lower section having a top side, a flexible saw contacting the top side of at least some of said lower sections and adapted to be located beneath said sternum, said saw adapted to extend substantially in the direction of said incision.

2. The combination of claim 1 wherein at least one portion of said saw is adapted to extend to said upper side of said sternum.

3. The combination of claim 2 wherein at least a part of said portion is adapted to be located between at least one of said upper sections and said upper side of said sternum.

4. The combination of claim 1 wherein each of said lower sections comprises a lower grip adapted to extend across said incision and having a lower gripping means adapted to engage said lower side of said sternum, each of said upper sections comprises an upper grip adapted to extend across said incision and having an upper gripping means adapted to engage said upper side of said sternum, a stem having a lower end adapted to engage said lower grip and further adapted to project through said sternum and said upper grip, means on said stem for urging said lower grip and said upper grip into clamping relationship with said sternum.

5. The combination of claim 4 wherein said lower gripping means comprises a plurality of upstanding teeth.

6. The combination of claim 4 wherein said upper gripping means comprises a plurality of depending teeth.

7. The combination of claim 4 wherein said stem is threaded, and said means for urging comprises threads mating with the threads on each of said stems.

8. The combination of claim 4 wherein said stem is threaded, and said means for urging comprises a nut on each of said stems above said upper grip and adapted, when turned with relation to said stem, to bear against said upper grip.

9. The combination of claim 4 wherein said means for urging comprises threads on said stem engaging said upper grip, said stem being freely rotatable with respect to said lower grip, whereby rotation of said stem causes said upper grip to move toward said lower grip.

10. The combination of claim 4 wherein at least one said upper grip comprises a bridge extending upwardly therefrom and having an opening therein adapted to permit said stem to extend therethrough.

11. The combination of claim 10 wherein said opening engages threads on said stem.

12. The combination of claim 4 wherein at least one groove is provided in an upper surface of said lower grip, said saw being therein.

13. The combination of claim 12 wherein said flexible saw is at least partially within a tube and said tube is at least partially in said groove.

14. The combination of claim 12 wherein said lower grip has two grooves spaced apart in a direction substantially parallel to said incision whereby, when tension is placed on said saw, said lower grip is urged into a position wherein said gripping means is on both sides of said incision.

15. The combination of claim 4 wherein said stem, at an upper end remote from said lower end, carries a loop, and a rod removably extending through said loop.

16. The combination of claim 4 wherein said lower grip and said upper grip are provided with a plurality of holes therethrough.

17. The combination of claim 4 wherein said at least one of said upper grip, said lower grip, and said stem are at least partially comprised of absorbable surgical polymer.

18. The combination of claim 4 wherein said flexible saw is coated with absorbable surgical polymer.

19. The combination of claim 1 wherein said flexible saw is at least partially within a tube.

20. The combination of claim 1 wherein at least some of said fastening means is capable of being absorbed by the body.

21. A combination of a saw and a device for securing a sternum in a closed position after opening, said sternum having an upper side and a lower side, said device comprising at least one fastening means, adapted to be located along an incision;

each said fastening means comprising a lower grip, adapted to be located beneath said sternum, and adapted to extend across said incision, and having a gripping means adapted to engage said lower side of said sternum, an upper grip adapted to be located on top of said sternum, and adapted to extend across said incision, and having an upper gripping means adapted to engage said upper side of said sternum, a stem having a lower end adapted to engage said lower grip and further adapted to project upwardly through said sternum and said upper grip, said stem having threads which engage at least said upper grip, and adapted, when turned relative to said stem, to move said upper grip toward said lower grip, each lower grip including a top side, a flexible saw contacting the top side of said lower grip and adapted to fit beneath said sternum, said saw extending substantially in the same direction as said incision, there being portions of said saw adapted to extend to said upper side, at least a part of said portions adapted to be adjacent said upper side, said stem carrying a loop at an upper end remote from said lower end, a rod removably extending through said loop, whereby said fastening means can be positioned prior to engagement with said sternum.

22. A method of treating a sternum after opening, said sternum having an upper side and a lower side, said method comprising closing said sternum, anchoring a plurality of fastening means to said sternum spaced apart along an incision, whereby lower sections of at least some of said fastening means extend beneath said sternum and said fastening means also have upper sections extending on said upper side of said sternum, placing a flexible saw beneath said sternum, between said lower sections and said lower side of said sternum, and substantially along said incision.

23. The method of claim 22 comprising placing at least one portion of said saw on said upper side of said sternum.

24. The method of claim 23 further comprising placing at least a part of said portion between at least one of said upper sections and said upper side of said sternum.

25. The method of claim 23 further comprising gripping said saw by said portion and manipulating said saw by said portion to cause reciprocation thereof.

26. The method of claim 22 further comprising reopening said sternum by reciprocating said saw, whereby said saw cuts through said sternum.

27. The method of claim 22 further comprising clamping said sternum between said lower section and said upper section.

28. The method of claim 22 wherein each of said lower sections comprises a lower grip extending across said incision, each of said upper sections comprises an upper grip extending across said incision, each of a plurality of stems has a lower end adapted to engage said lower grip and further adapted to project upwardly through said sternum and said upper grip, said method further comprising urging said lower grip and said upper grip into clamping relationship with said sternum.

29. The method of claim 28 wherein said stems are threaded and said means for urging is a nut on said stem which engages said thread and bears against said upper grip, further comprising tightening said nut to bring said upper grip and said lower grip into clamping relationship with said sternum.

30. The method of claim 28 wherein there are threads engaging said upper grip on at least one of said stems, said at least one of said stems being freely rotatable with respect to said lower grip, said method comprising rotating said stem relative to said upper grip whereby said upper grip is moved toward said lower grip.

31. The method of claim 28 further comprising removing a length of at least one of said stems extending above said upper grip after said urging into clamping relationship.

32. The method of claim 28 wherein at least one said upper grip comprises a bridge extending upwardly therefrom and having an opening therein to permit said stem to extend therethrough, said method comprising, on reopening said sternum, cutting said bridge and removing said upper grip.

* * * * *